US009381370B2

(12) United States Patent
Gunderson (10) Patent No.: US 9,381,370 B2
(45) Date of Patent: Jul. 5, 2016

(54) METHOD AND APPARATUS FOR DETERMINING PARAMETERS FOR OVERSENSING IN AN IMPLANTABLE MEDICAL DEVICE

(71) Applicant: Medtronic, Inc., Minneapolis, MN (US)

(72) Inventor: Bruce D Gunderson, Plymouth, MN (US)

(73) Assignee: Medtronic, Inc., Minneaplis, MN (US)

( * ) Notice: Subject to any disclaimer, the term of this patent is extended or adjusted under 35 U.S.C. 154(b) by 0 days.

(21) Appl. No.: 14/511,917

(22) Filed: Oct. 10, 2014

(65) Prior Publication Data

US 2016/0074666 A1    Mar. 17, 2016

Related U.S. Application Data (60) Provisional application No. 62/049,130, filed on Sep. 11, 2014.

(51) Int. Cl.
*A61N 1/39* (2006.01)
*A61B 5/0402* (2006.01)
*A61B 5/04* (2006.01)

(52) U.S. Cl.
CPC ............ *A61N 1/3925* (2013.01); *A61B 5/0402* (2013.01); *A61B 5/04012* (2013.01)

(58) Field of Classification Search
CPC .. A61N 1/3925; A61B 5/0412; A61B 5/0402; A61B 5/7235; A61B 5/7271; A61B 5/7264; A61B 5/046; A61B 5/0464
See application file for complete search history.

(56) References Cited

U.S. PATENT DOCUMENTS

| 5,179,945 | A | 1/1993 | Van Hofwegen et al. |
| 5,188,105 | A | 2/1993 | Keimel |
| 5,403,354 | A | 4/1995 | Adams et al. |
| 5,458,619 | A | 10/1995 | Olson |
| 6,169,923 | B1 | 1/2001 | Kroll |
| 6,625,490 | B1 | 9/2003 | McClure et al. |
| 6,862,476 | B2 | 3/2005 | Mouchawar et al. |
| 7,027,858 | B2 | 4/2006 | Cao et al. |
| 7,283,863 | B2 | 10/2007 | Gunderson et al. |
| 7,333,855 | B2 | 2/2008 | Gunderson et al. |
| 7,398,123 | B1 | 7/2008 | Levine |
| 7,496,403 | B2 | 2/2009 | Cao et al. |
| 7,756,570 | B1 | 7/2010 | Bornzin |
| 7,783,354 | B2 | 8/2010 | Gunderson |
| 7,813,798 | B2 | 10/2010 | Bornzin et al. |
| 7,831,304 | B2 | 11/2010 | Cao et al. |
| 8,064,996 | B2 | 11/2011 | Belk et al. |
| 8,068,901 | B2 | 11/2011 | Ghanem et al. |
| 8,175,708 | B1 | 5/2012 | Snell et al. |
| 8,265,756 | B1 | 9/2012 | Snell et al. |

(Continued)

FOREIGN PATENT DOCUMENTS

WO    2006104849 A1    10/2006

*Primary Examiner* — Paula J Stice (57) ABSTRACT

A method and medical device for determining oversensing that includes sensing cardiac signals from a first sensing channel, determining whether oversensing of the cardiac signal is occurring in response the cardiac signals sensed from the first sensing channel, determining a sensing parameter adjustment and initiating sensing of cardiac signals from a second sensing channel having the adjusted sensing parameter in response to oversensing being determined to occur, determining an oversensing value in response to the sensing in the second sensing channel, and storing the determined oversensing value.

19 Claims, 6 Drawing Sheets

(56) References Cited

U.S. PATENT DOCUMENTS

| | | |
|---|---|---|
| 8,521,281 B2 | 8/2013 | Patel et al. |
| 8,565,865 B2 | 10/2013 | Belk et al. |
| 8,694,097 B2 | 4/2014 | Cao et al. |
| 2008/0161870 A1 | 7/2008 | Gunderson |
| 2008/0215110 A1 | 9/2008 | Gunderson |
| 2009/0292331 A1 | 11/2009 | Gunderson et al. |
| 2009/0299201 A1 | 12/2009 | Gunderson |
| 2010/0049271 A1 | 2/2010 | Hofstadter et al. |
| 2010/0280567 A1 | 11/2010 | Gunderson |
| 2011/0196247 A1 | 8/2011 | Cao et al. |
| 2012/0071944 A1 | 3/2012 | Gunderson et al. |
| 2013/0138004 A1 | 5/2013 | Dong et al. |
| 2013/0289644 A1 | 10/2013 | Martinez et al. |

| Sensitivity Adjustment | Secondary Sensing SIC (ave/day) | Primary Sensing SIC (ave/day) |
|---|---|---|
| 0.45 mV  450 | 23  456 | 125  462 |
| 0.60 mV | 0.2 | 130 |
| Vector Adjustment  452 | 458 | 462 |
| Tip (26) to Ring (20) | 128 | 128 |
| Blanking Period Adjustment  454 | 460 | 462 |
| 130 ms | 119 | 127 |
| 140 ms | 103 | 126 |
| 150 ms | 92 | 131 |

FIG. 6

METHOD AND APPARATUS FOR DETERMINING PARAMETERS FOR OVERSENSING IN AN IMPLANTABLE MEDICAL DEVICE

CROSS-REFERENCE TO RELATED APPLICATIONS

This application claims the benefit of U.S. Provisional Application No. 62/049,130, filed on Sep. 11, 2014. The disclosure of the above application is incorporated herein by reference in its entirety.

TECHNICAL FIELD

The disclosure relates generally to implantable medical devices and, in particular, to a method and device for determining parameters for oversensing in an implantable medical device.

BACKGROUND

Implantable medical devices are available to provide therapies for restoring normal cardiac rhythms by delivering electrical shock therapy for cardioverting or defibrillating the heart in addition to cardiac pacing. Such a device, commonly known as an implantable cardioverter defibrillator or "ICD", delivers an appropriate therapy, such as cardiac pacing, upon detecting an abnormal rhythm. Cardiac pacing is delivered in response to the absence of sensed intrinsic depolarizations, referred to as P-waves in the atrium and R-waves in the ventricle. In response to tachycardia detection, a number of tiered therapies may be delivered beginning with anti-tachycardia pacing therapies and escalating to more aggressive shock therapies until the tachycardia is terminated. Termination of a tachycardia is commonly referred to as "cardioversion." Ventricular fibrillation (VF) is a serious life-threatening condition and is normally treated by immediately delivering high-energy shock therapy. Termination of VF is normally referred to as "defibrillation."

In modern implantable cardioverter defibrillators, the physician programs the particular anti-arrhythmia therapies into the device ahead of time, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected. For an overview of tachycardia detection and treatment therapies reference is made to U.S. Pat. No. 5,545,186 issued to Olson et al.

Detection of tachycardia or fibrillation may also trigger the storage of the sensed intracardiac electrogram (EGM) for a period of several seconds such that the EGM signals leading up to and during a detected arrhythmia episode are available for downloading and displaying on an external programmer or other device for analysis by a physician. Such analysis aids the physician in monitoring the status of the patient and the patient's response to delivered therapies. Occasionally, cardioversion or defibrillation therapies are delivered when the patient does not feel symptomatic. In such cases, the ICD may inappropriately detect a tachycardia or fibrillation episode that does not exist and deliver an anti-arrhythmia therapy when it is not needed. Inappropriate arrhythmia detection is generally caused by oversensing, which can be defined as the sensing of events other than the one P-wave and/or the one R-wave occurring during each normal sinus cardiac cycle. Oversensing of both cardiac and non-cardiac events can result in inappropriate arrhythmia detection by the ICD if the detected rate due to oversensing falls into an arrhythmia detection zone. Oversensing can also impact the timing of pacing algorithms and in some causes may withhold life sustaining pacing therapy for pacemaker dependent patients when oversensing occurs over a long period of time (e.g. myopotentials). Cardiac oversensing refers to oversensing of cardiac events such as far-field P-waves, T-waves, or R-waves that are sensed twice and are therefore "double-counted".

Anti-tachycardia pacing therapies delivered during normal sinus rhythm can potentially induce an arrhythmia in some patients, making the delivery of a therapy in response to inappropriate arrhythmia detection highly undesirable. Therefore, what is needed is a method and apparatus for reducing instances of oversensing.

DETAILED DESCRIPTION

The present invention is aimed at providing a system and method for automatically identifying and trouble-shooting cardiac and/or non-cardiac oversensing by an implantable cardiac stimulation device. The methods included in the present invention may be used in conjunction with, or incorporated in, an implantable cardiac stimulation device such as a pacemaker or an implantable cardioverter defibrillator (ICD), a subcutaneously implanted device, or other monitoring devices, capable of storing sensed intracardiac electrogram (EGM) data.

Figure 1:
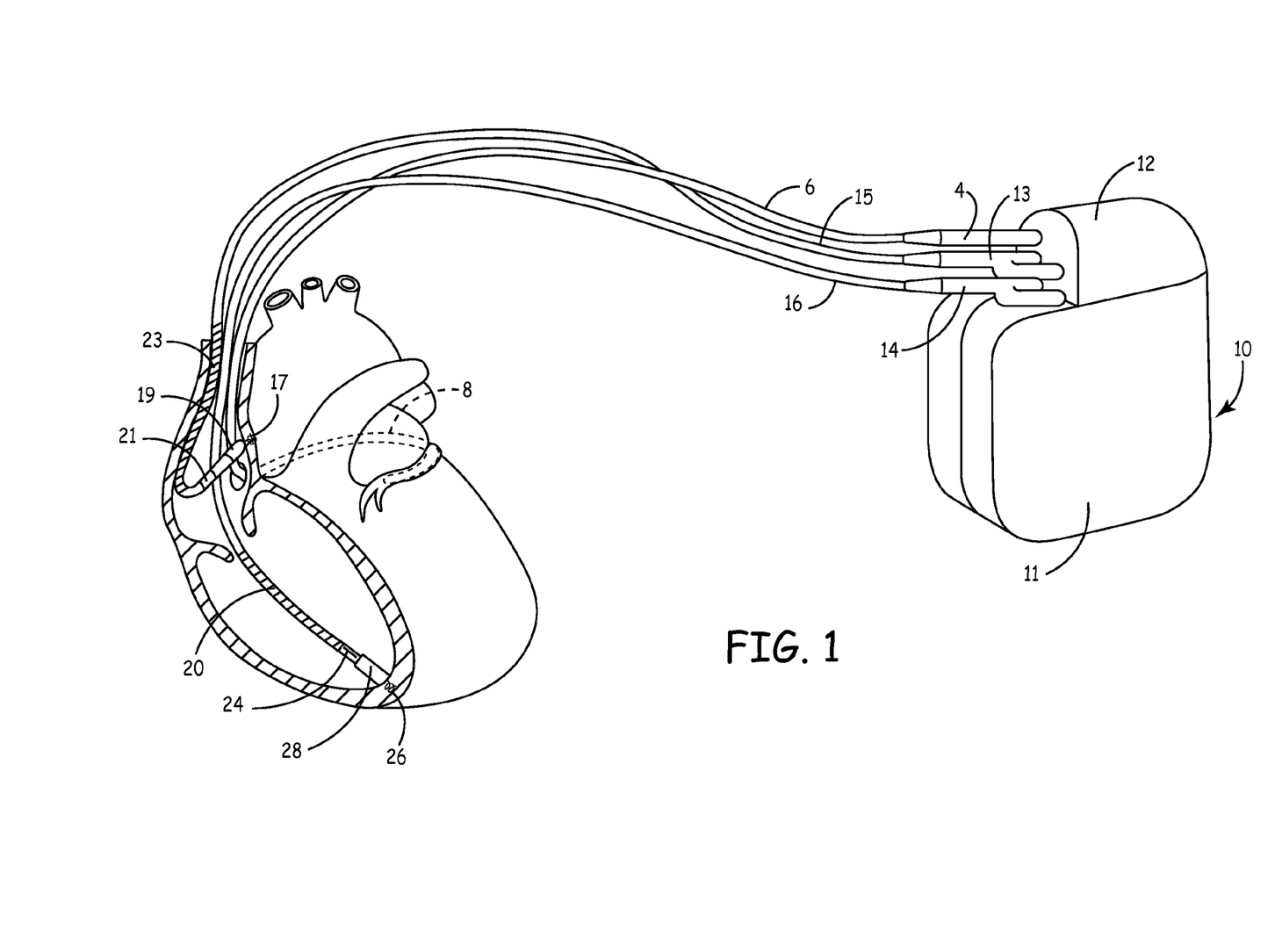
FIG. 1 is a schematic diagram of an exemplary medical device for determining oversensing according to the present disclosure.

FIG. 1 is a schematic diagram of an exemplary medical device for determining oversensing according to an embodiment of the present disclosure. As illustrated in FIG. 1, a medical device according to an embodiment of the present disclosure may be in the form of an implantable cardioverter defibrillator (ICD) 10 a connector block 12 that receives the proximal ends of a right ventricular lead 16, a right atrial lead 15 and a coronary sinus lead 6, used for positioning electrodes for sensing and stimulation in three or four heart chambers. Right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, or other cardiac monitoring device.

Figure 2:
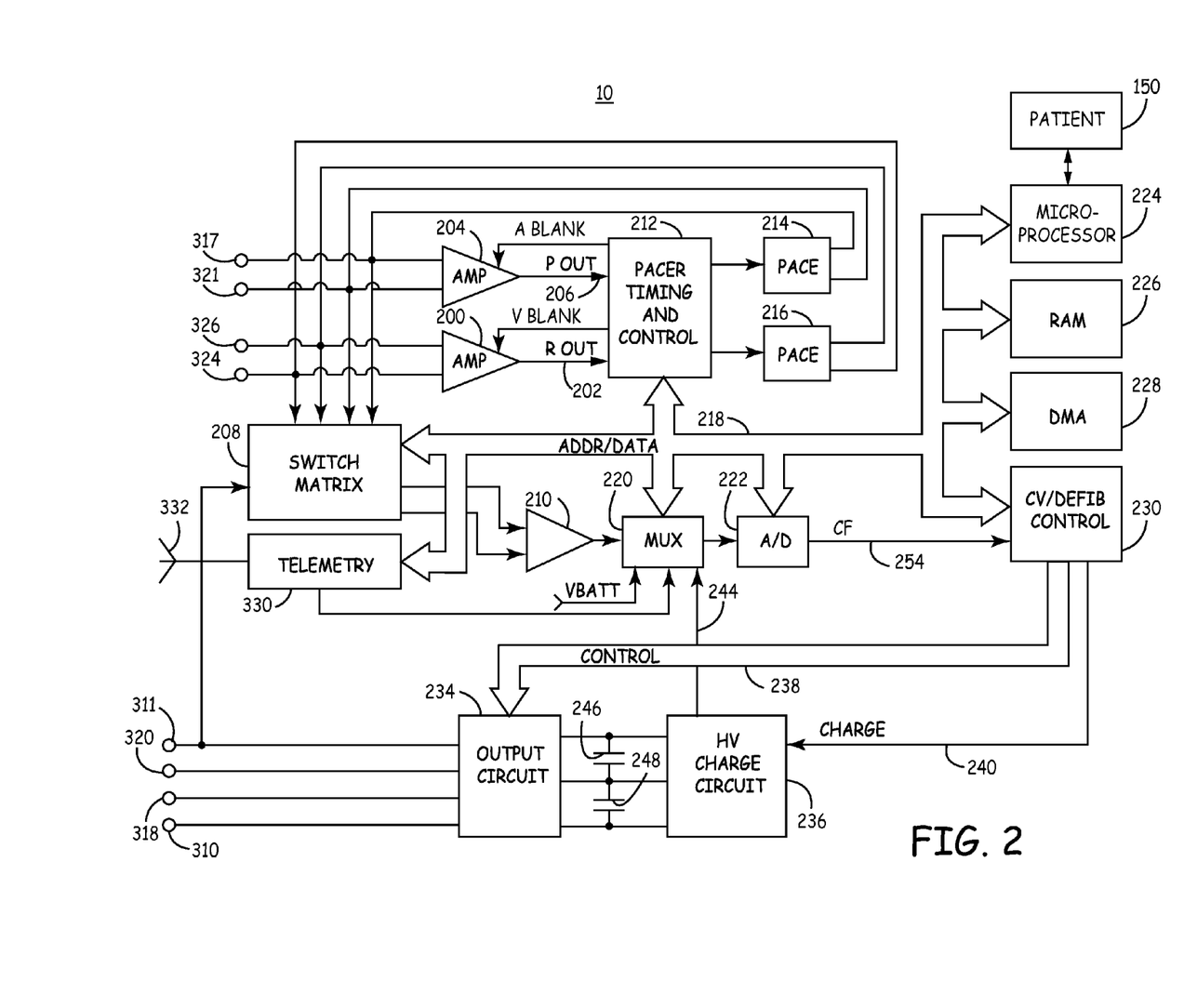
FIG. 2 is a functional schematic diagram of the medical device of FIG. 1.

FIG. 2 is a functional schematic diagram of the medical device of FIG. 1. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensitivity. In accordance with the invention, ICD 10 and, more specifically, microprocessor 224 automatically adjusts the sensitivity of atrial sense amplifier 204, ventricular sense amplifier 200 or both in response to detection of oversensing in order to reduce the likelihood of oversensing. Ventricular sense amplifier 200 and atrial sense amplifier 204 operate in accordance with originally programmed sensing parameters for a plurality of cardiac cycles, and upon detecting oversensing, automatically provides the corrective action to avoid future oversensing. In this manner, the adjustments provided by ICD 10 to amplifiers 200 and 204 to avoid future oversensing are dynamic in nature. Particularly, microprocessor 224 increases a sensitivity value of the amplifiers, thus reducing the sensitivity, when oversensing is detected. Atrial sense amplifier 204 and ventricular sense amplifier 200 receive timing information from pacer timing and control circuitry 212. Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock. As will be described, the blanking periods of atrial sense amplifier 204 and ventricular sense amplifier 200 and, in turn, the blanking periods of sensing electrodes associated with the respective amplifiers may be automatically adjusted by ICD 10 to reduce the likelihood of oversensing. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Specifically, microprocessor 224 may modify the electrode configurations based on detection of oversensing due to cardiac or non-cardiac origins. Upon detection of R-wave oversensing, for example, microprocessor 224 may modify the electrode configuration of the right ventricle from true bipolar sensing, e.g., tip-to-ring, to integrated bipolar sensing, e.g., tip-to-coil.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy, incorporated herein by reference in its entirety. Annotation of sensed events, which may be displayed and stored with EGM data, is described in U.S. Pat. No. 4,374,382 issued to Markowitz, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
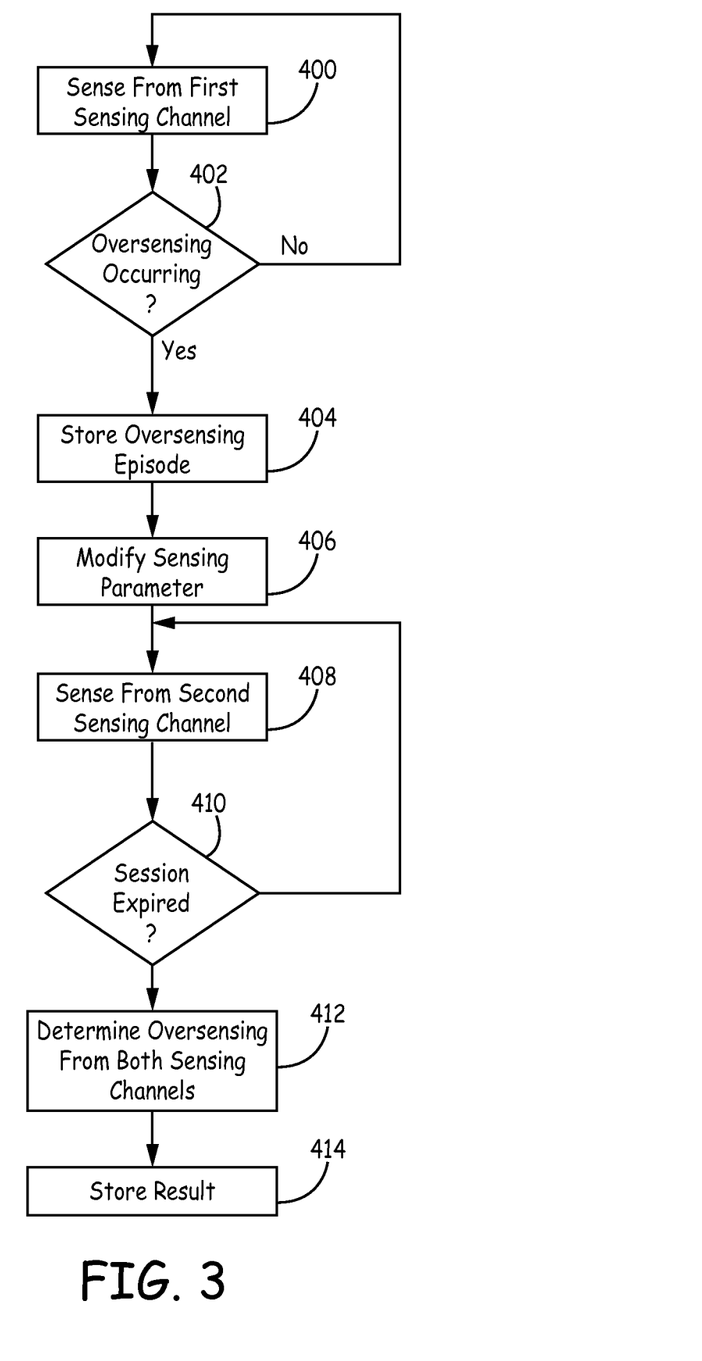
FIG. 3 is a flowchart of a method of determining oversensing in a medical device according to an embodiment of the present disclosure.

FIG. 3 is a flowchart of a method of determining oversensing in a medical device according to an embodiment of the present disclosure. As illustrated in FIG. 3, according to an embodiment of the present disclosure, during normal sensing operation, the device senses cardiac signals using a predetermined primary sensing channel, such as the sensing channel formed between electrodes 24 and 26 of FIG. 1, utilizing ventricular sense amplifier 200, to determine whether an arrhythmia event is occurring and whether delivery of therapy by the device is appropriate, Block 400. In addition, the device analyses EGM data associated with the sensing of Block 400 to determine the occurrence of sensed interval patterns that are indicative of specific types of oversensing, including both cardiac and non-cardiac types of oversensing, Block 402. Various types of cardiac oversensing that may be identified include, but are not limited to, far-field R-wave oversensing, R-wave oversensing, and T-wave oversensing. Non-cardiac causes of oversensing that may be diagnosed include electromagnetic interference, non-cardiac myopotentials, a lead fracture, or a poor lead connection.

For example, according to one embodiment, the device may determine whether T-wave oversensing is occurring, using the method of determining T-wave oversensing as described, for example, in U.S. Pat. No. 7,831,304 to Gillberg, et al., incorporated herein by reference in it's entirety. According to another embodiment, the device may determine oversensing using a sensing integrity counter, as described, for example, in U.S. Pat. No. 7,369,893 to Gunderson, incorporated herein by reference in it's entirety.

Figure 4:
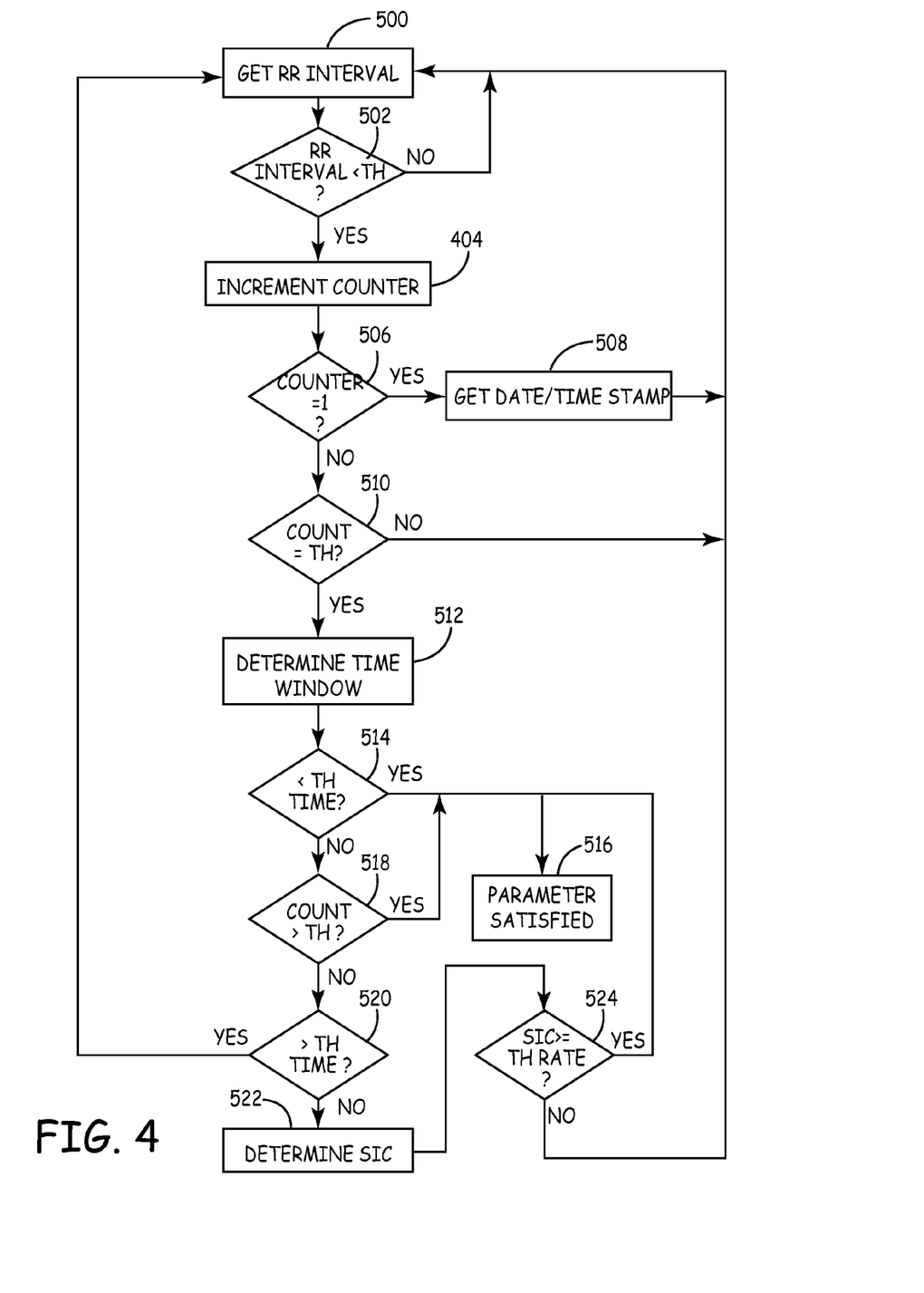
FIG. 4 is a flowchart of an exemplary method for determining whether an oversensing criteria has been satisfied, according to an embodiment of the present disclosure.

FIG. 4 is a flowchart of an exemplary method for determining whether an oversensing criteria has been satisfied, according to an embodiment of the present disclosure. As illustrated in FIG. 4, according to an embodiment of the present disclosure, in order to determine whether oversensing is occurring in Block 402 using a sensing integrity counter, the device determines a next RR-interval, Block 500, and a determination is made as to whether the RR-interval is less than a predetermined threshold, Block 502. According to one embodiment, the device counts the number of RR-intervals that are determined to be less than a predetermined threshold, such as 140 ms, for example, although any desired threshold may be utilized.

If the RR-interval is not less than the predetermined threshold, and therefore is not near the blanking period, a next RR-interval is obtained, Block 500, and a determination is made as to whether the next RR-interval is less than the predetermined threshold, Block 503. Each time that the current RR-interval is determined to be less than the predetermined threshold, a counter is incremented, Block 504. If the current RR-interval is the initial RR-interval for the current session, i.e., the counter is equal to one in Block 506, a date/time stamp since the last session is obtained from the timing and control circuitry 212, for example, to determine a start time of the current session, Block 508.

Once the session start time is determined, a next RR-interval is obtained, Block 500, and the process is repeated, with a determination being made as to whether the next RR-interval is less than the predetermined threshold, Block 502. If the current RR-interval is not the initial RR-interval, i.e., the counter is not equal to one in Block 506, a determination is made as to whether the number of RR-intervals that are less than the threshold in Block 502, is equal to a predetermined threshold number, Block 510. If less than the predetermined threshold number of RR-intervals are less than the threshold, NO in Block 510, a next RR-interval is obtained, Block 500, and the process is repeated, with a determination being made as to whether the next RR-interval is less than the predetermined threshold, Block 502.

Once the number of RR-intervals is equal to the predetermined threshold number, YES in Block 510, a current time window duration is determined by taking the difference between the start time of the current session obtained in Block 508 and the current date/time stamp obtained from the timing and control circuitry 212, Block 512. Once the current time window duration is determined, a determination is made as whether the current time window duration is less than or equal to a threshold time window, Block 514. If the time duration window is less than or equal to the threshold time window, the oversensing criteria is determined to be satisfied, Block 516, and therefore the criteria counter is incremented.

According to an embodiment of the present invention, the predetermined threshold number utilized in Block 510 is set equal to thirty and the threshold time window is set equal to three days for Block 514, so that one way in which the oversensing criteria is satisfied and therefore the oversensing criteria counter is incremented is if thirty RR-intervals are determined to be near the blanking period within the first three days, for example. However, any desired values for the predetermined threshold number of Block 510 and the threshold time window of Block 514 without departing from the present invention. According to the present invention, the predetermined threshold number utilized in Block 510 is given a value corresponding to an indication that a mechanical problem associated with the lead is present, such as a loose set screw, and is therefore set equal to thirty, for example, although any desired value may be utilized. In addition, although three days is utilized in Block 514, any desired number of days or other time period may be utilized.

If the time duration window is greater than the threshold time window, NO in Block 514, a determination is made as to whether the number of RR-intervals determined to be less than 140 ms during the current session is greater than a second predetermined threshold number, Block 518, by determining whether the counter in Block 514 is greater than the second predetermined threshold number of Block 518. According to an embodiment of the present invention, the second predetermined threshold number of Block 518 is set as 300, for example, although any threshold value may be chosen. If the number of RR-intervals less than 140 ms is greater than the second threshold, the oversensing criteria is determined to be satisfied, Block 516, and the criteria counter is incremented. If the number of RR-intervals less than 140 ms is less than or equal to the second threshold, No in Block 518, a determination is made as to whether the time duration window is greater than a second threshold time period, such as 30 days, for example, Block 520.

If the time duration window is not greater than the second threshold time period, an average sensing integrity counter per day is determined, Block 522, by dividing the count of the number of RR-intervals determined to be near the blanking period, Block 504, by the current time window duration determined in Block 512. A determination is then made as to whether the average sensing integrity counter per day is greater than or equal to a predetermined threshold rate, such as 10 per day, for example, Block 524, although the predetermined threshold rate in Block 524 could have any desired value associated with an indication of a lead-related condition. If the average sensing integrity counter per day is greater than or equal to the predetermined threshold rate, the oversensing criteria is determined to be satisfied, Block 516, and therefore the criteria counter is incremented. If average sensing integrity counter per day is not greater than or equal to the predetermined threshold rate, a next RR-interval is obtained, Block 500, and the process is repeated with a determination being made as to whether the next RR-interval is less than the predetermined threshold, Block 502.

Finally, if the number of RR-intervals less than the 140 ms threshold is less than or equal to the second threshold, No in Block 518, and the time duration window is greater than the second threshold time period, YES in Block 520, a next RR-interval is obtained, Block 500, and the process is repeated with a determination being made as to whether the next RR-interval is less than the predetermined threshold, Block 502.

Returning to FIG. 3, once oversensing is determined to be occurring from the signal sensed by the primary sensing channel, Yes in Block 402, the device stores the resulting oversensing detection episode, Block 404, and then modifies one or more parameters of the second sense amplifier 210 impacting sensing, such as the blanking period, the sensitivity, or the sensing vector utilized, Block 406, for example. The device then continues sensing the cardiac signal from the sensing vector utilized during normal sensing, Block 400, i.e., electrode 24 and 26, using the primary sense amplifier 200 and continues determining oversensing, Block 402, and simultaneously senses the cardiac signal, Block 408, from the same sensing vector, i.e., electrode 24 and 26, using the secondary sense amplifier 210 and the modified parameter or parameters form Block 406 for a predetermined session time period, such as one week, for example. Once the session time period has expired, Yes in Block 410, the device determines a corresponding oversensing value for both the primary sensing channel and the secondary sensing channel during the session time period, Block 412, and stores the oversensing values, Block 414. According to one embodiment, the session time period is set as one week, although other desired time periods may be utilized, such as two weeks or a month, for example.

For example, in an embodiment where the determination as to whether oversensing was occurring was made in the primary sensing channel in Block 402 by determining a sensing integrity counter, as described above, and where the primary setting of the sensitivity for the primary sensing channel is set as 0.30 millivolts, the device may modify the sensitivity utilized by the secondary sense amplifier by a predetermined amount, such as 0.15 millivolts, for example, so that the sensitivity for the second sense amplifier 210 is set as 0.45 millivolts, Block 406. In this way, sensing of the signal is simultaneously performed in the primary channel using the primary sensitivity setting of 0.30 millivolts and in the secondary channel using the adjusted sensitivity setting of 0.45 millivolts. If the session time period of Block 410 is set as one week, once the session time period has expired, Yes in Block 410, the device determines oversensing for both sensing channels by dividing the resulting sensing integrity counter values for each of the sensing channels by one week, i.e., seven days, to get a resulting sensing integrity counter value for each sensing channel, Block 412, that is then stored, Block 414. The stored result can subsequently be viewed by a clinician to determine if there is a reduction in oversensing as a result of the parameter modification in Block 406, i.e., modifying the sensitivity from 0.30 millvolts to 0.45 millivolts. For example, if the sensing integrity value over the one week session time period for the primary sensing channel is 770, resulting in a sensing integrity counter value of 110 per day, and the sensing integrity value over the one week session time period for the secondary sensing channel is 161, resulting in a sensing integrity counter value of 23 per day, the clinician can decide whether the change in sensitivity is appropriate, and therefore elect whether or not to subsequently adjust the sensitivity in the primary sensing channel from 0.30 millivolts to 0.45 millivolts.

According to another embodiment, rather than modifying the sensitivity of the secondary sensing channel in Block 406, the device may modify the blanking period. For example, if the blanking period utilized in the primary sensing channel is set as 120 ms, the device may modify the blanking period utilized by the secondary sense amplifier 210 by a predetermined amount, such as 10 ms for example, so that the blanking period for the secondary sense amplifier 210 is set as 130 ms, Block 406. In this way, sensing of the signal is simultaneously performed in the primary channel using the primary blanking period setting of 120 ms and in the secondary channel using the adjusted blanking period setting of 130 ms. If the session time period of Block 410 is set as one week, once the session time period has expired, Yes in Block 410, the device determines oversensing for both sensing channels by dividing the resulting sensing integrity counter values for each of the sensing channels by one week, i.e., seven days, to get a resulting sensing integrity counter value for each sensing channel, Block 412, that is then stored, Block 414. The stored result can subsequently be viewed by a clinician to determine if there is a reduction in oversensing as a result of the parameter modification in Block 406, i.e., modifying the blanking period from 120 ms to 130 ms, and to then decide whether the change in blanking period is appropriate, and therefore elect whether or not to subsequently adjust the blanking period in the primary sensing channel from 120 ms to 130 ms.

Similarly, according to another embodiment the device may modify the sensing vector. For example, if the sensing vector utilized in the primary sensing channel between electrode 24 and electrode 26, the device may modify the sensing vector utilized by the secondary sense amplifier 210 to be between electrode 26 and electrode 20, for example, Block 406. In this way, sensing of the signal is simultaneously performed in the primary channel using electrode 24 and electrode 26 and in the secondary channel using electrode 26 and electrode 20. If the session time period of Block 410 is set as one week, once the session time period has expired, Yes in Block 410, the device determines oversensing for both sensing channels by dividing the resulting sensing integrity counter values for each of the sensing channels by one week, i.e., seven days, to get a resulting sensing integrity counter value for each sensing channel, Block 412, that is then stored, Block 414. The stored result can subsequently be viewed by a clinician to determine if there is a reduction in oversensing as a result of the parameter modification in Block 406, i.e., modifying the sensing vector from electrode 24 and 26 to electrode 26 and 20, and to then decide whether the change in sensing vector is appropriate, and therefore elect whether or not to subsequently adjust the sensing vector in the primary sensing channel from electrode 24 and electrode 26 to electrode 26 and electrode 20.

While the adjusted sensing parameter is described as being either the sensitivity, blanking period or sensing vector, other parameters impacting sensing may be utilized in the same way if desired.

Figure 5:
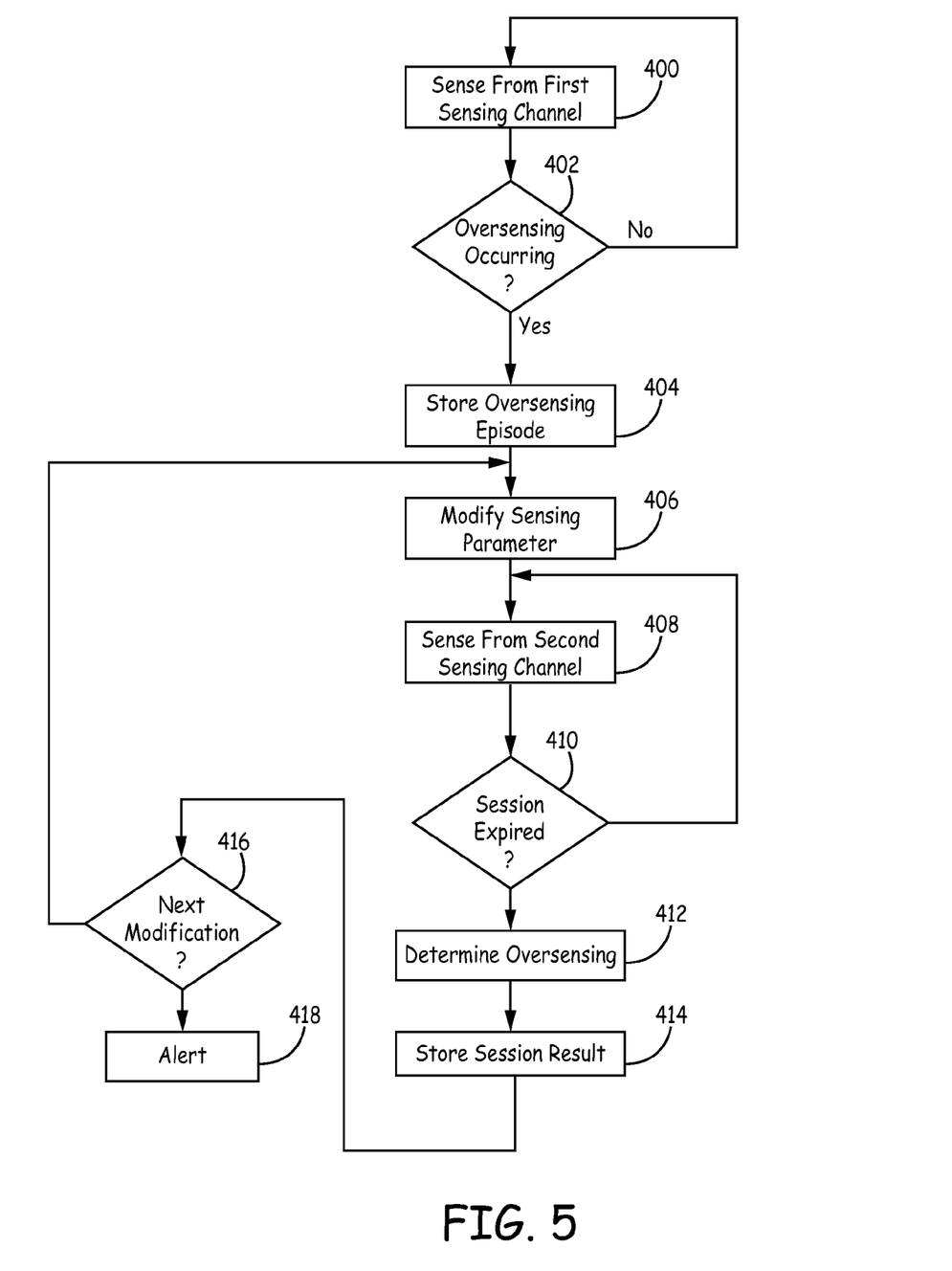
FIG. 5 is a flowchart of a method of determining oversensing in a medical device according to an embodiment of the present disclosure.
Figure 6:
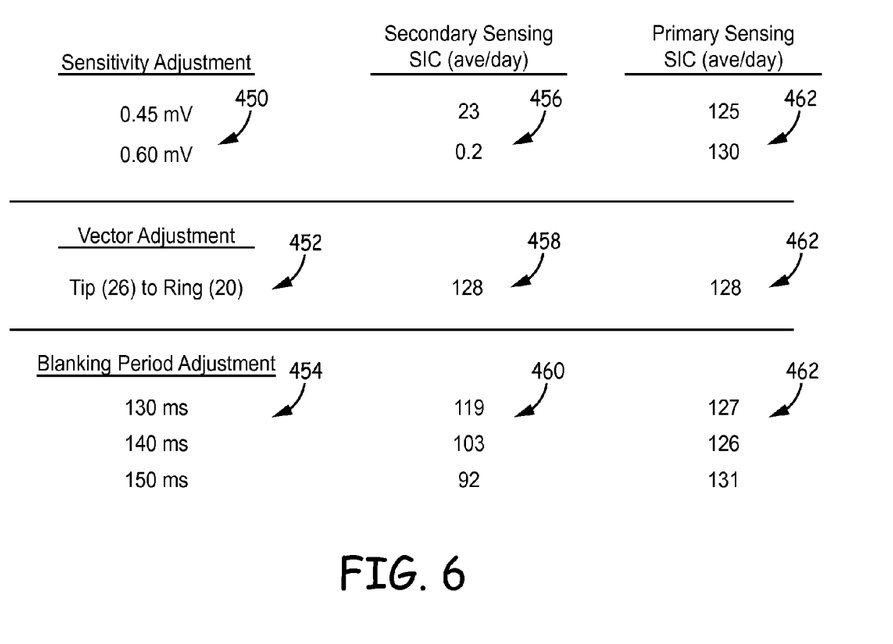
FIG. 6 is a schematic diagram of the stored result of the sensing parameter modification to determine adjustment in parameters for during determining of oversensing according to an embodiment of the disclosure.

FIG. 5 is a flowchart of a method of determining oversensing in a medical device according to an embodiment of the present disclosure. According to other embodiments, the device may make multiple determinations for a given parameter, or may make multiple determinations for multiple parameters in any combination or combinations desired. For example, as illustrated in FIG. 6, in an embodiment where the device modifies the sensitivity utilized by the second sense amplifier, once the session time period for the adjusted parameter is expired, Yes in Block 412, and the result is stored, the device determines whether an additional sensing parameter modification is to be made, Block 416. If an additional modification to the sensing parameter is to be made, Yes in Block 416, the device further modifies the sensitivity utilized by the secondary sense amplifier by the predetermined amount, i.e., 0.15 millivolts so that the sensitivity for the second amplifier is set as 0.60 millivolts, Block 406.

In this way, sensing of the signal is simultaneously performed in the primary channel using the primary sensitivity setting of 0.30 millivolts and in the secondary channel using the adjusted sensitivity setting of 0.60 millivolts. If the session time period of Block 410 is set as one week, once the session time period has expired, Yes in Block 410, the device determines oversensing for both sensing channels by dividing the resulting sensing integrity counter values for each of the sensing channels by one week, i.e., seven days, to get a resulting sensing integrity counter value for each sensing channel, Block 412, that is then stored, Block 414. The stored result of both modifications of the sensitivity can subsequently be viewed by a clinician to determine if there is a reduction in oversensing as a result of the parameter modifications in Block 406, i.e., modifying the sensitivity from 0.30 millivolts to 0.45 millivolts and to 0.60 millivolts, and to decide whether either change in sensitivity is appropriate, and therefore elect whether or not to subsequently adjust the sensitivity in the primary sensing channel from 0.30 millivolts to 0.45 millivolts or to 0.60 millivolts.

According to another embodiment where the device modifies the blanking period utilized by the second sense amplifier, once the session time period for the adjusted parameter is expired, Yes in Block 412, and the result is stored, the device determines whether an additional sensing parameter modification is to be made, Block 416. If an additional modification to the sensing parameter is to be made, Yes in Block 416, the device further modifies the blanking period utilized by the secondary sense amplifier by the predetermined amount, i.e., 10 ms, so that the blanking period for the second amplifier is set as 140 ms, Block 406.

In this way, sensing of the signal is simultaneously performed in the primary channel using the primary blanking period setting of 120 ms and in the secondary channel using the adjusted blanking period setting of 140 ms. If the session time period of Block 410 is set as one week, once the session time period has expired, Yes in Block 410, the device determines oversensing for both sensing channels by dividing the resulting sensing integrity counter values for each of the sensing channels by one week, i.e., seven days, to get a resulting sensing integrity counter value for each sensing channel, Block 412, that is then stored, Block 414. The stored result of both modifications of the blanking period can subsequently be viewed by a clinician to determine if there is a reduction in oversensing as a result of the parameter modifications in Block 406, i.e., modifying the blanking period from 120 ms to 130 ms and to 140 ms, and to decide whether either change in blanking period is appropriate, and therefore elect whether or not to subsequently adjust the blanking period in the primary sensing channel from 120 ms to 130 ms or to 140 ms.

FIG. 6 is a schematic diagram of the stored result of the sensing parameter modification to determine adjustment in parameters for during determining of oversensing according to an embodiment of the disclosure. As illustrated in FIG. 6, according to another embodiment, the device may perform modifications combinations of any two or all three of the sensing parameters. For example, in the determination of whether to perform a next modification in Block 416 of FIG. 5, the device may make one or more adjustments to two of the sensing parameters or to all three parameters. In the example illustrated in FIG. 6, the device makes two adjustments to the sensitivity parameter 450, one adjustment to the sensing vector 452, and three adjustments to the blanking period 454 in the secondary sense amplifier. In this way, the stored results 456-460 output from the secondary sense amplifier 210 of all of the adjustments of the sensitivity 450, the blanking period 454 and the sensing vector 452 can subsequently be viewed by a clinician to determine if there is a reduction in oversensing, compared to the results 462-466 of the simultaneous sensing of the cardiac signal in the primary sensing channel, as a result of the multiple sensing parameter adjustments in Block 406, and to decide whether either a change in any or a combination of all of the parameters is appropriate, and therefore elect whether or not to subsequently adjust one or more of the parameters.

While the method and apparatus of the present disclosure has been described above using the example where the device determines oversensing by determining a sensing integrity counter, it is understood that the method described above may also be utilized when other types of cardiac oversensing determinations are performed by the device, such as T-wave oversensing, far-field R-wave oversensing, R-wave oversensing, or when other types of non-cardiac causes of oversensing are performed, such as electromagnetic interference, non-cardiac myopotentials, a lead fracture, or a poor lead connection, for example.

In addition, according to an embodiment of the disclosure, the device may automatically adjust the sensitivity in the primary sensing channel based on the result of the stored output from the secondary sense amplifier 210 based on adjustment to one or more sensing parameters exceeding a predetermined threshold. For example, in an embodiment where an adjustment to the sensitivity is made in the secondary sense channel, the device would determine if the resulting sensing integrity output from the secondary channel is less than a predetermined threshold, such as 1, for example. If the resulting output from the secondary channel is less than the predetermined threshold, i.e., less than 1, the device would subsequently adjust the sensitivity in the primary sensing channel accordingly.

According to another embodiment, additional EGM storage could also occur when oversensing occurs on the primary sensing channel but not on the secondary sensing channel as evidence that the oversensing was eliminated or subsided.

Thus, a method and apparatus for determining oversensing in a medical device have been presented in the foregoing description with reference to specific embodiments. It is appreciated that various modifications to the referenced embodiments may be made without departing from the scope of the disclosure as set forth in the following claims.

I claim:

1. A method of determining oversensing in a medical device, comprising:
sensing cardiac signals from a first sensing channel comprising a primary sense amplifier;
determining whether oversensing of the cardiac signal is occurring in response the cardiac signals sensed from the first sensing channel;
determining a sensing parameter adjustment and initiating sensing of cardiac signals from a second sensing channel comprising a secondary amplifier and having the adjusted sensing parameter in response to the oversensing being determined to occur;
determining a first oversensing value in response to the sensing in the first sensing channel and a second oversensing value in response to the sensing in the second sensing channel; and
storing the determined first oversensing value and the determined second oversensing value.

2. The method of claim 1, further comprising:
comparing the first oversensing value to the second oversensing value; and
determining whether to subsequently adjust the sensing parameter in response to the comparing.

3. The method of claim 1, further comprising:
incrementing a sensing integrity counter in response to cardiac signals sensed from the first sensing channel; and
determining whether oversensing of the cardiac signal is occurring in response the incremented sensitivity integrity counter.

4. The method of claim 3, further comprising:
comparing the first oversensing value to the second oversensing value; and
determining whether to subsequently adjust the sensing parameter in response to the comparing.

5. The method of claim 1, wherein the adjusted sensing parameter comprises one of a sensitivity, a blanking period, and a sensing vector.

6. The method of claim 5, further comprising:
comparing the first oversensing value to the second oversensing value; and
determining whether to subsequently adjust the sensing parameter in response to the comparing.

7. The method of claim 1, further comprising:
determining whether the determined oversensing value satisfies an oversensing value threshold; and
performing the sensing parameter adjustment in the primary sensing channel in response to the oversensing value satisfying the oversensing value threshold.

8. The method of claim 7, further comprising:
incrementing a sensing integrity counter in response to cardiac signals sensed from the first sensing channel; and
determining whether oversensing of the cardiac signal is occurring in response the incremented sensitivity integrity counter.

9. The method of claim 8, wherein the adjusted sensing parameter comprises one of a sensitivity, a blanking period, and a sensing vector.

10. A medical device, comprising:
a plurality of electrodes for sensing cardiac signals;
a first sense amplifier sensing cardiac signals via an electrode of the plurality of electrodes and a second sense amplifier via the electrode of the plurality of electrodes;
a storage device; and
a processor configured to determine whether oversensing of the cardiac signal is occurring in response the cardiac signals sensed via the first sense amplifier, determine a sensing parameter adjustment and initiate sensing of cardiac signals via the second sensing amplifier having the adjusted sensing parameter in response to the oversensing being determined to occur, determine a first oversensing value in response to the cardiac signals sensed via the first sense amplifier and a second oversensing value in response to the cardiac signals sensed via the second sense amplifier, and store the determined first oversensing value and the determined second oversensing value in the storage device.

11. The device of claim 10, wherein the processor is further configured to compare the first oversensing value to the second oversensing value; and
determine whether to subsequently adjust the sensing parameter in response to the comparing.

12. The device of claim 10, wherein the processor is further configured to increment a sensing integrity counter in response to cardiac signals sensed via the first sense amplifier, and determine whether oversensing of the cardiac signal is occurring in response the incremented sensitivity integrity counter.

13. The device of claim 12, wherein the processor is further configured to compare the first oversensing value to the second oversensing value; and
determine whether to subsequently adjust the sensing parameter in response to the comparing.

14. The device of claim 10, wherein the adjusted sensing parameter comprises one of a sensitivity, a blanking period, and a sensing vector.

15. The device of claim 14, wherein the processor is further configured to compare the first oversensing value to the second oversensing value; and
determine whether to subsequently adjust the sensing parameter in response to the comparing.

16. The device of claim 10, wherein the processor is further configured to determine determining whether the determined oversensing value satisfies an oversensing value threshold, and perform the sensing parameter adjustment in the first sense amplifier in response to the oversensing value satisfying the oversensing value threshold.

17. The device of claim 16, wherein the processor is further configured to increment a sensing integrity counter in response to cardiac signals sensed via the first sense amplifier, and determine whether oversensing of the cardiac signal is occurring in response the incremented sensitivity integrity counter.

18. The device of claim 17, wherein the adjusted sensing parameter comprises one of a sensitivity, a blanking period, and a sensing vector.

19. A non-transitory, computer-readable storage medium storing instructions for causing a processor included in a medical device to perform a method for determining oversensing, the method comprising:
sensing cardiac signals from a first sensing channel comprising a primary sense amplifier;
determining whether oversensing of the cardiac signal is occurring in response the cardiac signals sensed from the first sensing channel;
determining a sensing parameter adjustment and initiating sensing of cardiac signals from a second sensing channel comprising a secondary amplifier and having the adjusted sensing parameter in response to the oversensing being determined to occur;
determining a first oversensing value in response to the sensing in the first sensing channel and a second oversensing value in response to the sensing in the second sensing channel; and
storing the determined first oversensing value and the determined second oversensing value.

* * * * *